(12) United States Patent
Tu et al.

(10) Patent No.: US 8,658,159 B2
(45) Date of Patent: Feb. 25, 2014

(54) METHOD TO INDUCE AND EXPAND THERAPEUTIC ALLOANTIGEN-SPECIFIC HUMAN REGULATORY T CELLS IN LARGE-SCALE

(75) Inventors: Wenwei Tu, Ap Lei Chau (HK); Yu-Lung Lau, Hong Kong (HK); David Bram Lewis, Stanford, CA (US)

(73) Assignees: Versitech Limited, Hong Kong (HK); The Board of Trustees of the Leland Stanford Junior University, Palo Alto, CA (US)

( * ) Notice: Subject to any disclaimer, the term of this patent is extended or adjusted under 35 U.S.C. 154(b) by 272 days.

(21) Appl. No.: 12/432,964

(22) Filed: Apr. 30, 2009

(65) Prior Publication Data

US 2009/0324557 A1 Dec. 31, 2009

Related U.S. Application Data

(60) Provisional application No. 61/133,643, filed on Jun. 30, 2008.

(51) Int. Cl.
*A01N 63/00* (2006.01)
*C12N 5/071* (2010.01)
*C12N 5/00* (2006.01)
*C12N 5/02* (2006.01)

(52) U.S. Cl.
USPC ............... 424/93.71; 435/372.3; 435/373; 435/377

(58) Field of Classification Search
None
See application file for complete search history.

(56) References Cited

U.S. PATENT DOCUMENTS

| 2005/0186207 A1* | 8/2005 | Bluestone et al. ......... 424/144.1 |
| 2006/0115899 A1 | 6/2006 | Buckner et al. |
| 2007/0172947 A1 | 7/2007 | Shirwan |

FOREIGN PATENT DOCUMENTS

| CA | 2446391 | 4/2005 |
| EP | 1870452 | 12/2007 |
| WO | 2006050138 | 5/2006 |
| WO | WO 2006090291 A2 * | 8/2006 |
| WO | 2006107850 | 10/2006 |
| WO | 2006127152 | 11/2006 |
| WO | 2007067683 | 6/2007 |
| WO | 2007167683 | 6/2007 |
| WO | 2007110785 | 10/2007 |
| WO | 2007125362 | 11/2007 |

OTHER PUBLICATIONS

Schultze et al., 1997, J. Clin. Invest. vol. 100: 2757-2765.*
Baecher-Allan et al., 2001, J. lmmmunol. vol. 167: 1245-1253.*
von der Weid et al., 2001, Clin. Diagn. Lab. Immunol. vol. 8: 695-701.*
Schlienger et al., 2000, Blood. vol. 96: 3490-98.*

* cited by examiner

*Primary Examiner* — Amy Juedes
(74) *Attorney, Agent, or Firm* — Turocy & Watson, LLP

(57) ABSTRACT

Methods for inducing, expanding, and/or generating alloantigen-specific regulatory T cells. Alloantigen-specific regulatory T cells can be induced, expanded, and/or generated from naive CD4$^+$CD25$^-$ T cells by using CD40-activated B cells. The regulatory T cells can be human T cells. In one embodiment, the alloantigen-specific human regulatory T cells can be CD4$^{high}$CD25$^+$Foxp3$^+$ regulatory T cells.

6 Claims, 6 Drawing Sheets

METHOD TO INDUCE AND EXPAND THERAPEUTIC ALLOANTIGEN-SPECIFIC HUMAN REGULATORY T CELLS IN LARGE-SCALE

CROSS-REFERENCE TO RELATED APPLICATIONS

This application claims the benefit of priority to U.S. Provisional Application Ser. No. 61/133,643 filed Jun. 30, 2008, the entire contents of which are hereby incorporated by reference.

STATEMENT REGARDING FEDERALLY SPONSORED RESEARCH OR DEVELOPMENT

This invention was made with United States government support under contract AI050153, awarded by the National Institutes of Health. The United States government has certain rights in this invention.

BACKGROUND

Treatment with immunosuppressive drugs is widely accepted as an effective treatment for bone marrow and solid organ transplantation to improve the graft survival. However, chronic rejection of transplants still has a considerable impact on the long term outcome. Moreover, many immunosuppressive drugs nonspecifically target the immune response, leading to unwanted side effects, such as weakened overall immune system. Thus, the goal in transplantation is the induction of a sustained state of specific tolerance to donor alloantigens with minimization or complete withdrawal of global immunosuppression.

$CD4^+CD25^+Foxp3^+$ regulatory T cells (Treg) are negative regulators of immune responses to self- and foreign-antigens and play a critical role in maintaining immune tolerance by suppressing pathological immune responses in autoimmune diseases, transplant allograft rejection, and graft-versus-host-disease (GVHD).[1-3] Upon adoptive transfer in rodents, Treg were found to control experimental autoimmune diseases,[4] inhibit GVHD[5,6] and prevent transplant allograft rejection,[7,8] indicating that Treg-based therapy has a great therapeutic potential for these diseases in humans.

An important obstacle to Treg-based therapy has been the limited numbers of these cells that are available, as only about 1-2% of circulating human $CD4^+$ T cells are Treg. Several groups have developed protocols to expand a large number of polyclonal $CD4^+CD25^+$ Treg in vitro with repeated stimulation by either CD3 and CD28 mAbs or artificial antigen-presenting cells (APC) for activation through CD3 and CD28, together with exogenous high-dose IL-2.[9-11] polyclonal Treg may cause global immune suppression.[4,7] In addition, since there are only few antigen-specific Treg in the population of the polyclonal Treg, very large numbers of non-specifically expanded Treg are required to inhibit bone-marrow allograft rejection in animal models.[12] All of these characteristics of polyclonal Treg hamper their clinical applications.

In contrast, adoptive transfer of antigen-specific Treg has been shown to prevent and treat T-cell-mediated inflammatory diseases with high efficiency. In animal models, small number of antigen-specific Treg can suppress experimental autoimmune diseases,[13] prevent GVHD and allograft rejection in bone marrow and solid organ transplantation.[14,15] Importantly, the transfer of antigen-specific Treg prevented target antigen-mediated T-cell responses such as GVHD and allograft rejection but did not compromise host general immunity including the graft-versus-tumor activity and anti-viral immunity.[5,15-17] Based on these studies, antigen-specific Treg has substantial promise for human immunotherapy.

The reliable induction and expansion of rare antigen-specific Treg is technically challenging. Currently, several protocols for murine antigen-specific Treg induction and expansion have been reported in which either purified $CD4^+CD25^-$ or $CD4^+CD25^+$ cells were co-cultured with autologous dendritic cells (DCs) pulsed with alloantigen in the presence of high-dose IL-2 or directly co-cultured with allogeneic DCs.[14,18-20] Similar protocol has also been reported for generation of human antigen-specific Treg recently.[21] In this protocol, antigen-specific $CD4^+CD25^+$ Treg can be generated by using the co-culture of $CD4^+CD25^-$ T cells with allogeneic monocyte-derived DCs. However, the large-scale in vitro expansion of alloantigen-specific Treg is difficult because of certain features of DCs. For example, DCs are relatively rare in peripheral blood and are usually derived from apheresis or marrow sources including monocytes.[22,23] Further, DCs are not homogeneous and include multiple subsets with different functional capacities.[24] Finally, there is no effective way to expand human DCs so far.[25] In addition, the current approaches to generate human DCs in vitro are expensive and laborious.[26]

Schultze et al. reported a simple and low-cost method to expand large number human CD40-activated B cells up to $10^{5,6}$-fold from human peripheral blood mononuclear cells (PBMC).[27] These expanded B cells are effective as APCs and can efficiently induce antigen-specific T cells and cytotoxic T lymphocytes.[26,27]

However, the art lacks an effective means of generating human antigen-specific Treg on a large scale. Thus, there exists a need in the art for a method of inducing or generating human antigen-specific Treg on a large scale.

SUMMARY

The present invention provides novel methods for the induction, expansion, and/or generation of alloantigen-specific regulatory T cells. Advantageously, the induction, expansion, and/or generation of the regulatory T cells can be performed on a large scale. The subject invention further provides cells produced according to the methods set forth herein.

In some embodiments, the subject invention provides novel protocols to induce and expand highly efficient human alloantigen-specific Treg in large-scale by co-culture of naïve $CD4^+CD25^-$ T cells with human allogeneic CD40-activated B cells without any exogenous cytokines. The induced alloantigen-specific Treg were $CD45RO^+$ and $CCR7^-$ memory cells, and expressed the common Treg markers (CD25 and Foxp3), as well as the lymph node homing receptor CD62L (L-selectin). They were also identifiable by a $CD4^{high}$ surface phenotype. The suppressive function of these $CD4^{high}CD25^+$ $Foxp3^+$ alloantigen-specific Treg was cell-cell contact dependent but did not involve cell-mediated cytotoxicity.

The methods of the subject invention for in vitro induction and expansion of alloantigen-specific Treg should facilitate the development of Treg-based clinical immunotherapy. For example, adoptive transfer of alloantigen-specific regulatory T cells can be used according to the subject invention for inhibiting allogeneic immune responses, e.g. GVHD, and preventing transplant allograft rejection. Additionally, methods of the present invention can be used to generate human alloantigen-specific Treg that can be used to control autoimmune diseases.

The methods of the subject invention are unique in their use of CD40-activated B cells as APCs rather than allogeneic monocyte-derived DCs or PBMC. CD40-activated B cells have an important advantage for this purpose in that they can be readily expanded in vitro to a relatively large numbers, while, in contrast, monocytes differentiating in vitro into dendritic cells do not undergo cell division. Cryopreserved CD40-activated B cells also retain their APC function upon thawing, and are relatively cost-effective to produce. In addition, because B cells stimulated with t-CD40-L cells or recombinant sCD40-L were equally effective at generating alloantigen-specific Treg, the use of sCD40-L significantly improves the clinical applicability of the procedure.

BRIEF DESCRIPTION OF THE FIGURES

The file of this patent contains at least one drawing executed in color. Copies of this patent with color drawings(s) will be provided by the Patent and Trademark Office upon request and payment of the necessary fee.

DETAILED DESCRIPTION

Figure 1:
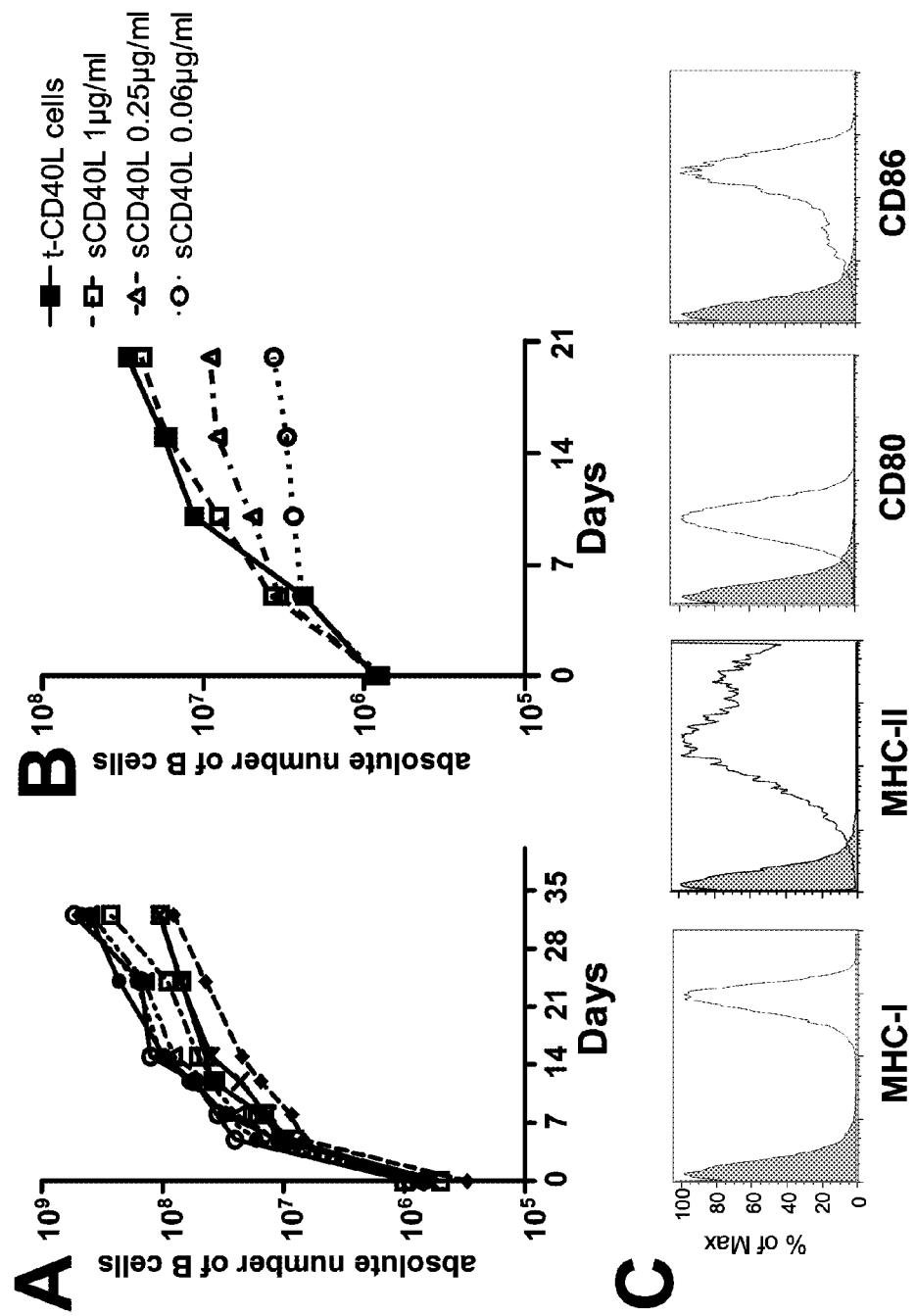
FIGS. 1A-C shows that CD40 activation is highly effective in generating large numbers of CD40-activated B cells that express high levels of MHC and co-stimulatory molecules. (1A) shows an overall expansion of CD40-activated B cells from 8 different individuals. CD40-activated B cells were generated by the co-culture of PBMC from 5 ml of peripheral blood with CD40L-transfected NIFI3T3 (t-CD40-L) cells. (1B) shows sCD40-L is as efficient as t-CD40-L cells at expanding human B cells in culture. CD40-activated B cells were generated by means of t-CD40-L cells or different concentrations of soluble hexameric CD4O-L. The results shown are representative of three independent experiments. (1C) shows expression of CD80, CD86, and MHC class I and II on the CD40-activated B cells cultured for 8 days (solid histograms). The filled histograms were obtained with relevant isotype controls. Data shown here are representative of B-cell populations obtained from 8 different healthy adult donors.

The present invention generally relates to methods for inducing, expanding, and/or generating alloantigen-specific regulatory 'T' cells (Treg). Advantageously, the induction, expansion, and/or generation of the regulatory T cells according to the subject invention can be performed on a large scale.

Methods of the subject invention provide simple, easy, low-cost, and novel protocols to obtain alloantigen-specific CD4$^{high}$CD25$^+$Foxp3$^+$ Treg from naive CD4$^+$CD25$^-$ T cells on a large scale by using allogeneic CD40-activated B cells. In preferred embodiments, the regulatory T cells are human T cells.

Advantageously, the alloantigen-specific Treg of the subject invention can be used to control autoimmune diseases and inhibit allogeneic immune responses, such as GVHD, and transplant allograft rejection.

Methods for CD4$^{high}$ Treg Cell Production

The subject invention provides relatively simple and low-cost protocols using allogeneic CD40-activated B cells to induce and expand highly efficient human alloantigen specific CD4$^{high}$CD25$^+$Foxp3$^+$ Treg from naive CD4$^+$CD25$^-$ T cells in large-scale. This facilitates clinical applications of Treg-based immunotherapy using in vitro induced and expanded alloantigen-specific Treg to induce donor-specific transplantation tolerance. Similar strategies, e.g. induction and expansion of autoantigen-specific Treg by using antigen-pulsed autologous CD40-activated B cells, can also be used in the treatment of autoimmune diseases in which the target self-antigens are known.

In one embodiment, a method of the invention comprises contacting a cell population that comprises naïve CD4$^+$CD25$^-$ T cells with a cell population that comprises allogeneic CD40-activated donor B cells for a period of time sufficient to generate donor alloantigenspecific regulatory T cells. T cells can optionally be isolated form the cell population following the contacting step. In one embodiment, the T cells are human T cells.

In a further embodiment, the cell population is contacted with CD40-activated B cells multiple times. In one embodiment, the alloantigen-specific human regulatory T cells can comprise CD4$^{high}$CD25$^+$Foxp3$^+$ regulatory T cells. In one embodiment, the alloantigen specific human regulatory T cells are CD4$^+$CD25$^+$ T cells. In one embodiment, a method of the invention further comprises expanding the population of alloantigen-specific human regulatory T cells generated using the present methods.

In contrast to prior work[26,27,43] in which autologous CD40-activated B cells were used as APCs in conjunction with IL-2 and IL-7 to generate effector T-cell responses, in accordance with the subject invention allogeneic Treg generation does not require the addition of exogenous cytokines. The absence of exogenous cytokines, such as IL-2 and IL-7, and using allogeneic rather than autologous CD40-activated B cells results in the differentiation and marked expansion of allogeneic Treg rather than effector T cells in the CD40-activated B cell/naive CD4$^+$ T-cell co-culture system.

Figure 6:
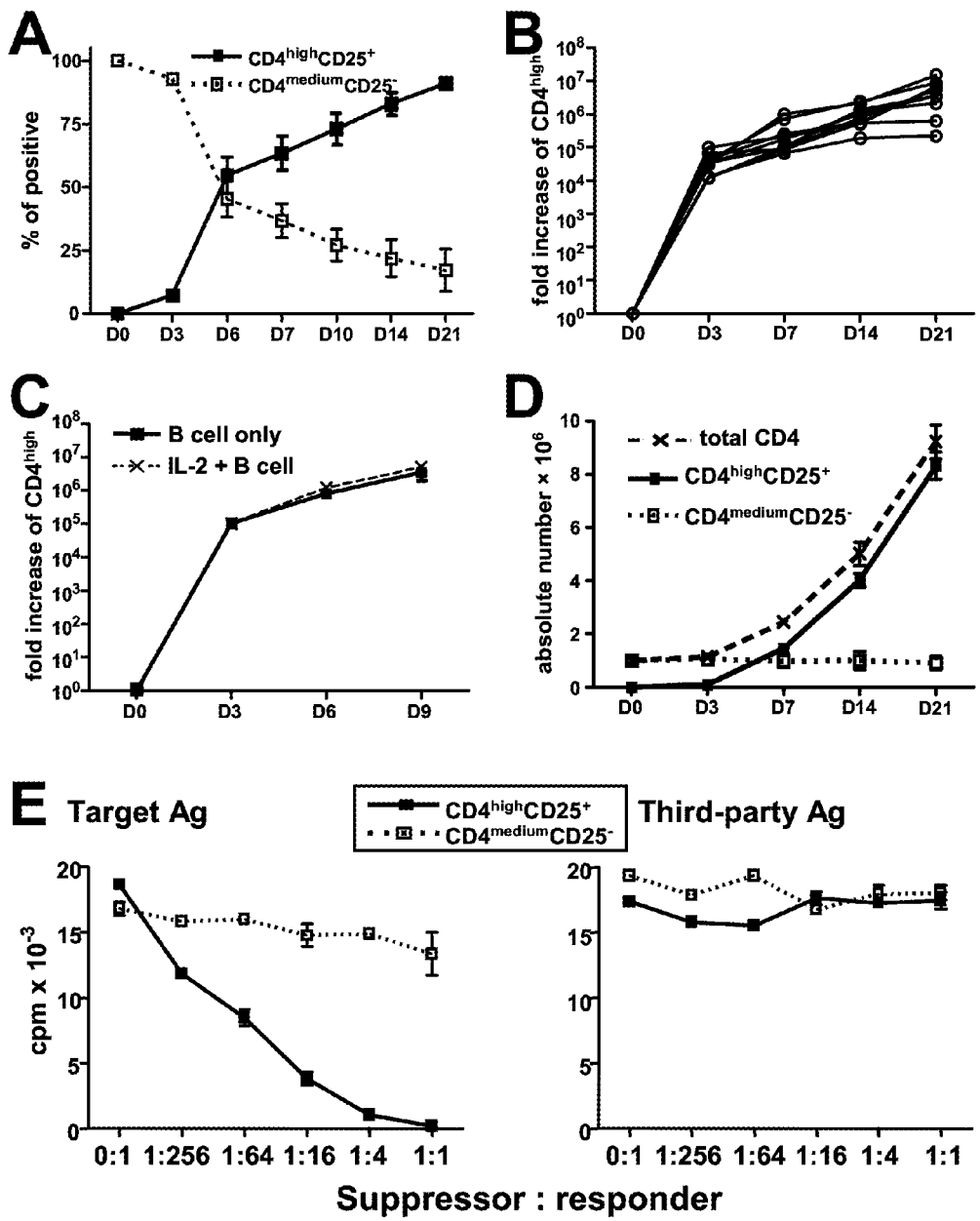
FIGS. 6A-E shows $CD4^{high}CD25^+$ alloantigen-specific Treg can be continuously expanded by CD40-activated B cells in large-scale without loss of function, and exogenous IL-2 does not enhance this cell expansion. Freshly purified naïve $CD4^+CD25^-$ T cells were co-cultured with CD40-activated allogeneic B cells for the indicated time. (6A) The percentages of CD4$^{high}$CD25$^+$ and CD4$^{medium}$CD25$^-$ cells in the cultures (n=10). (6B) Expansion of CD$_4^{high}$CD25$^+$ alloantigen-specific Treg from 10 different individuals. The expansion was normalized for the CD4$^{high}$CD25$^+$ cells, and the fold increase of the CD4$^{high}$CD25$^+$ was shown. (6C) Naïve CD4$^+$CD25$^-$ were co-cultured with CD40-activated allogeneic B cells with or without IL-2. The expansion was normalized for the CD4$^{high}$CD25$^+$ cells, and the fold increase of the CD4$^{high}$CD25$^+$ is shown (n=4). (6D) Absolute numbers of CD4$^{high}$CD25$^+$ alloantigen-specific Treg generated from 1×10$^6$ naïve CD4$^+$CD25$^-$ T cells (n=10). (6E) CD4$^{high}$CD25$^+$ alloantigen-specific Treg induced and expanded by CD40-activated B cells for 21 days remain functional. Freshly purified naïve CD4$^+$CD25$^-$ T cells (responder) were co-cultured with CD40-activated allogeneic B cells (target antigen) to induce and expand CD4$^{high}$CD25$^+$ Treg for 21 days with replacement of B cells every 7 days. The sorted CD4$^{high}$CD25$^+$ and CD4$^{medium}$CD25$^-$ cells were added into the MLR culture system as described in Materials and Methods. Data shown here are representative of three independent experiments.

Advantageously, in the culture system of the subject invention, it is unnecessary to add exogenous IL-2 for inducing and expanding alloantigen-specific CD4$^{high}$CD25$^+$Foxp3$^+$ Treg (FIG. 6D). This lack of a requirement for exogenous cytokines significantly reduces the cost for generation of alloantigen-specific Treg.

Figure 2:
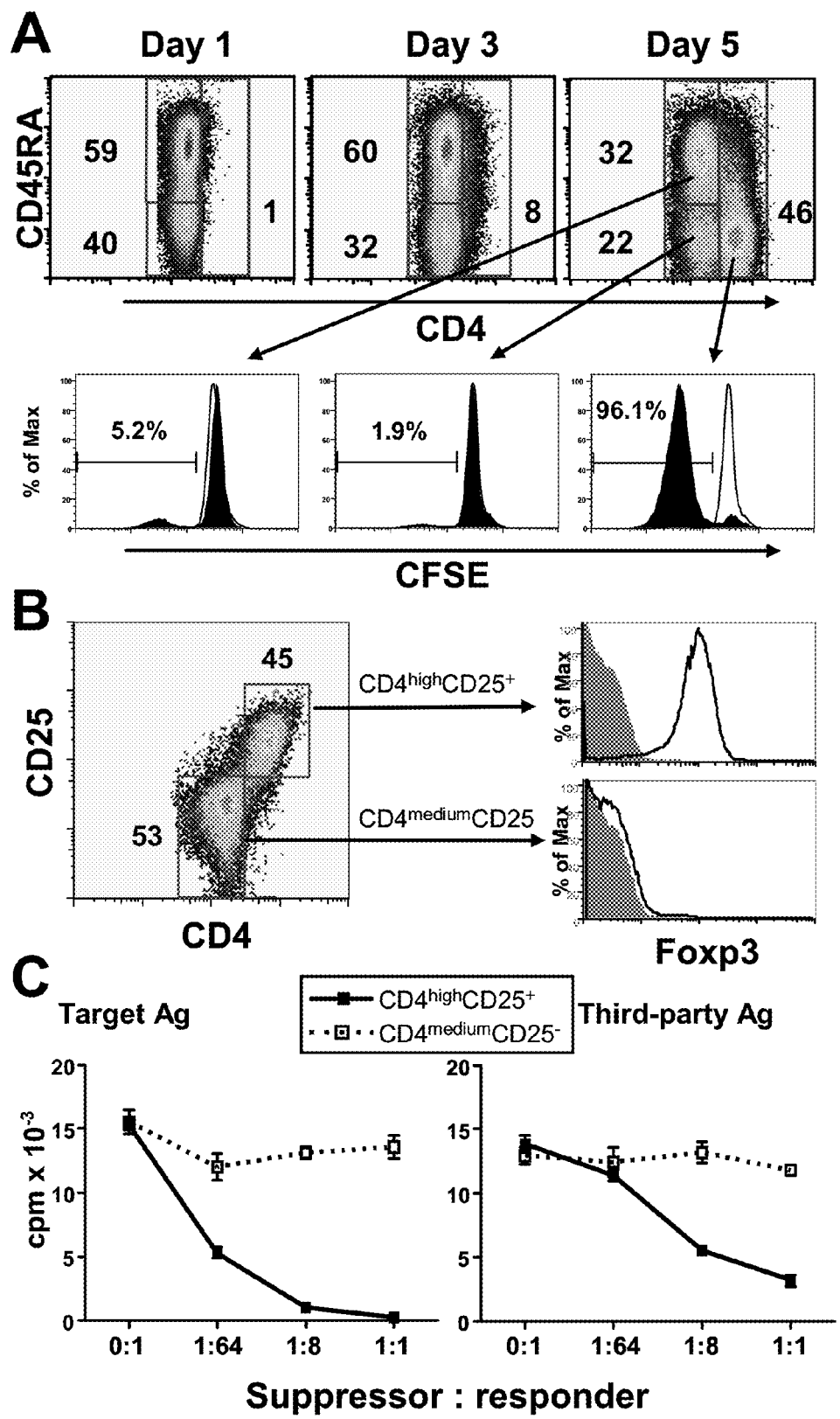
FIGS. 2A-C shows Human alloreactive $CD4^{high}$ cells induced by CD40-activated B cells are Treg. (2A) CD4 expression in $CD4^+CD25^-$ T cells stimulated with allogeneic B cells for 5 days (top panels), and its relationship with cell proliferation based on the loss of CFSE label and CD45RA expression. Top panels represented the T cells gated on CD4. The percentage of $CD4^+$ T cells in each gate is indicated. For the bottom panel, open histograms indicate the CFSE fluorescence intensities of the unstimulated control T cells, and the filled histograms represent the CFSE fluorescence intensities of the allostimulated T cells. The numbers in each histogram represent the percentage of cells that have undergone mitosis from each cell subset. (2B) $CD4^{high}$ cells express both CD25 and Foxp3. The dot plot on the left shows CD25 expression after 5 days of allostimulation. Open histograms on the right show the Foxp3 expression, and filled histograms indicate the isotype controls. The results shown are representative of four different experiments. (2C) $CD4^{high}CD25^+$ Treg generated from $CD4^+CD25^-$ T cells potently suppressed MLR in an antigen-nonspecific manner. Freshly purified $CD4^+CD25^-$ T cells were co-cultured with CD40-activated allogeneic B cells for 7 days. The sorted $CD4^{high}CD25^+$ (black squares) and $CD4^{medium}CD25^-$ (open squares) cells were added into MLR culture system as described in Materials and Methods. Proliferation (y-axis) is shown for 3 days of MLR. The results shown are representative of five different experiments.
Figure 3:
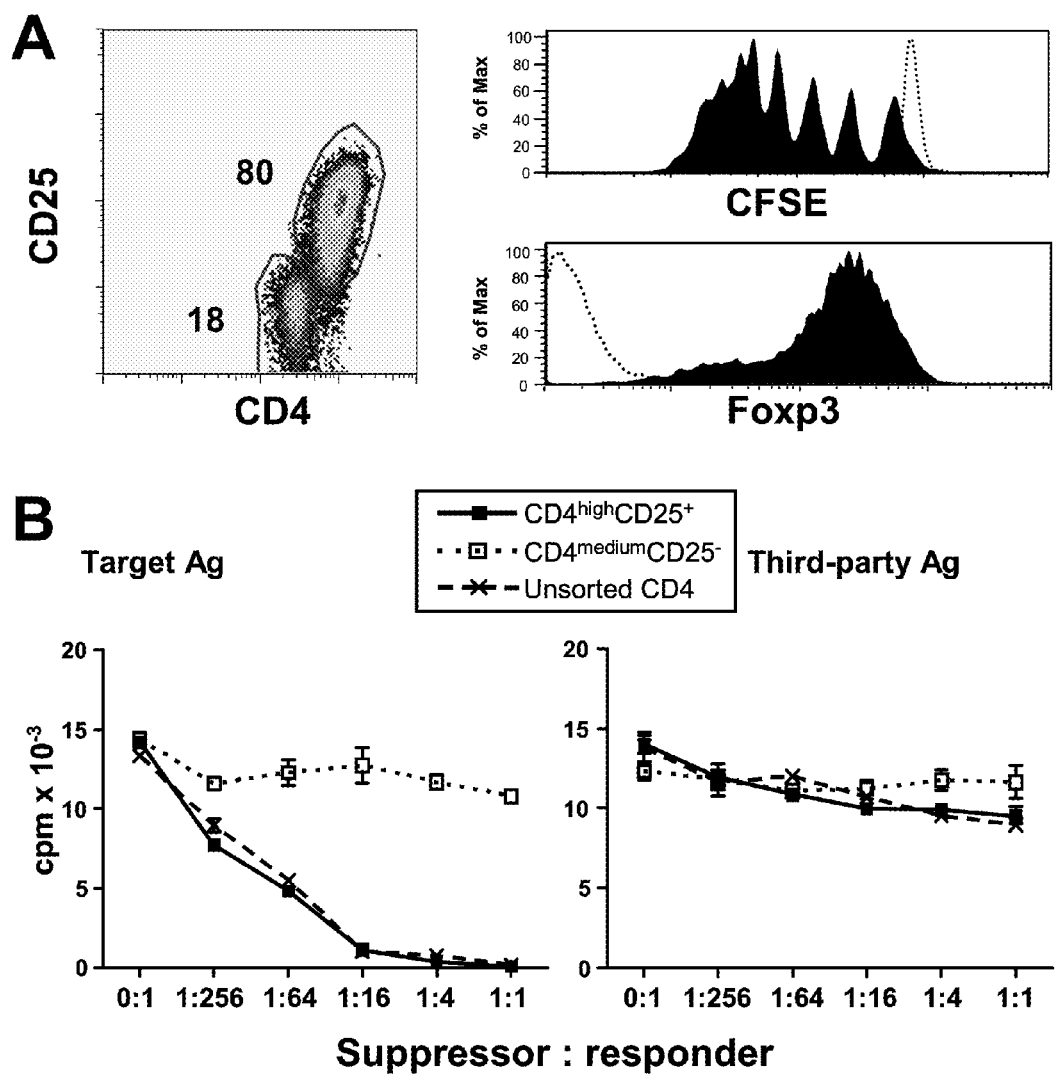
FIGS. 3A-B shows Human $CD4^{high}$ Treg induced from naïve $CD4^+CD25^-$ T cells by CD40-activated allogeneic B cells are alloantigen-specific Treg. (3A) Characteristics of $CD4^{high}$ Treg induced from naive $CD4^+CD25^-$ T cells. Freshly purified naive $CD4^+CD25^-$ T cells were labeled with CFSE and co-cultured with CD40-activated allogeneic B cells for 7 days. Representative data of CD4 and CD25 expression (left panel), CFSE dilution (right top panel) and Foxp3 expression (right bottom panel) from 6 independent experiments are shown. Open histograms show the CFSE fluorescence intensity (right top panel) and Foxp3 expression (right bottom panel) of $CD4^{medium}CD25^-$ cells. Filled histograms represent the CFSE fluorescence intensity (right top panel) and Foxp3 expression (right bottom panel) of $CD4^{high}CD25^+$ cells. (3B) $CD4^{high}CD25^+$ Treg generated from naïve $CD4^+CD25^-$ T cells potently suppressed MLR in an alloantigen-specific manner, and unsorted $CD4^+$ T cells generated from naïve $CD4^+CD25^-$ T cells had similar suppressor capacities in MLR. Freshly purified $CD4^+CD45RA^+CD25^-$ T cells were co-cultured with CD40-activated allogeneic B cells for 7 days. The sorted $CD4^{high}CD25^+$ (black squares) and $CD4^{medium}CD25^-$ (open squares), and unsorted $CD4^+$ T cells (crosses) were added into MLR culture system as described in Materials and Methods. Proliferation (y-axis) was shown for day 3 of MLR. The results shown are representative of 8 independent experiments.

In one embodiment, using a co-culture of allogeneic CD40-activated-B cells with total or naive CD4$^+$CD25$^-$ T cells, CD4$^{high}$CD25*Foxp3$^+$ Treg were generated after 5-7 days of culture (FIGS. 2-3). CD4$^{high}$CD25$^+$Foxp3$^+$ Treg generated from naive CD4$^+$CD25$^-$ T-cell precursors were alloantigen-specific (FIG. 3), whereas those derived from total CD4$^+$CD25$^-$ T cells, which included both naive and memory cells, had no antigen specificity (FIG. 2). Treg generated from memory CD4$^+$CD25$^-$T cells were also found to have no antigen specificity and could suppress both target and third-party antigen stimulated MLR. The reasons underlying the marked difference in antigen specificity between the Treg generated from total CD4$^+$CD25$^-$ and naive CD4$^+$CD25$^-$ T cells may be due to Treg generated from antigen-experienced memory cells present in total CD4$^+$CD25$^-$ T cells.

In one embodiment, about 6.4×10$^5$ to about 1.6×10$^7$ alloantigen-specific Treg can be generated from naive CD4$^+$CD25$^-$ T cells by repeated stimulation of allogeneic CD40-activated B cells for a period of time. The period of time can be, for example, from about 1 day to about 30 days. In one embodiment, the period of time is about 21 days.

The methods of the present invention can be used to generate, for example, from about 6×10$^6$ to about 1.1×10$^7$ alloantigen-specific Treg from every about 1×10$^6$ naïve CD4$^+$CD25$^-$ T cells. The naive CD4$^+$CD25$^-$ T cells can be obtained by, for example, being isolated from peripheral blood. In one embodiment, the naïve CD4$^+$CD25$^-$ T cells can be obtained by being isolated from about 5 milliliters (mL) to about 8 mL of peripheral blood.

Advantageously, unlike existing protocols for generating alloantigen-specific Treg using monocyte-derived allogeneic dendritic cells, methods of the present invention make it possible to expand alloantigen-specific Treg on a large scale. Methods of the subject invention also make it possible for alloantigen-specific Treg to be easily cryo-preserved and thawed for future use without loss of their functions. Additionally, the generation of CD40-activated-B cells used in the methods of the present invention is cost-effective. Moreover, the subject invention further reduces costs compared to existing methods since alloantigenspecific Treg can be generated without any exogenous recombinant cytokines.

Advantageously, the methods of the present invention for generating alloantigenspecific Treg do not suffer from the significant drawbacks of existing methods that utilize dendritic cells (DCs). For example, DCs are relatively rare in peripheral blood and are usually derived from apheresis or marrow sources including monocytes, and DCs are not homogeneous and represent different functionally-disparated cell types. Additionally, there is no known, effective way to expand human DCs, and the current approaches to generate human DCs in vitro are expensive and laborious.

CD4$^{high}$ Treg Cells

The subject invention also concerns isolated alloantigen-specific regulatory T cells generated using a method of the present invention. In one embodiment, the T cells are human T cells.

A significant upregulation of the CD4 molecule on T cells after the allostimulation of ïor total CD4$^+$CD25$^-$ T cells with allogeneic CD40-activated B cells was also observed. Based on the expression of CD4 and CD25, the allostimulated human CD4$^+$ T cells could be separated into two subsets: CD4$^{high}$CD25$^+$ and CD4$^{medium}$CD25$^-$ cells (FIGS. 2-3). The CD4$^{high}$CD25$^+$ but not CD4$^{medium}$CD25$^-$ cells were Treg that expressed Foxp3 and had highly suppressive capacities (FIGS. 2-3), raising the possibility that the CD4$^{high}$ might be a marker for human Treg in other contexts.

The alloantigen-specific CD4$^{high}$CD25$^+$Foxp3$^+$ Treg generated in the system or the subject invention were CD45RO$^+$ and CCR7$^-$ memory cells, and expressed high level of lymph node homing receptor CD62L (FIG. 3). These cells have the potential to be useful for migrating to peripheral lymphoid tissues draining graft sites to suppress T cell-mediated allograft rejection and GVHD. It has previously been demonstrated that ex vivo expanded Treg can retain their regulatory activity and migrate appropriately into the peripheral lymphoid organs in the recipient if they express a high level of CD62L.[12,47]

Figure 4:
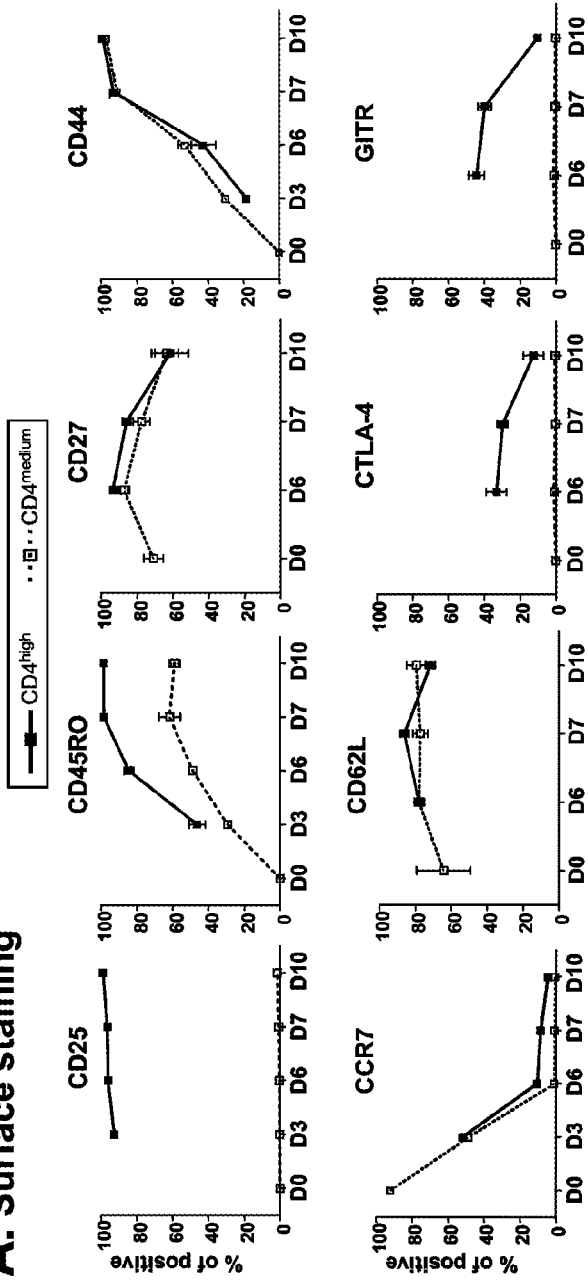
FIGS. 4A-B shows characteristics of $CD4^{high}CD25^+$ alloantigen-specific Treg. Freshly purified naïve $CD4^+CD25^-$ T cells were co-cultured with CD40-activated allogeneic B cells for the indicated time. The expression of cell surface markers (4A) and intracellular cytokines (4B) were determined and analyzed by FACS as described in Materials and Methods. The percentage of positive cells for each cell surface marker or intracellular cytokine within the $CD4^{high}CD25^+$ and $CD4^{medium}CD25^-$ subsets are indicated. The results shown are representative of four independent experiments.
Figure 4:
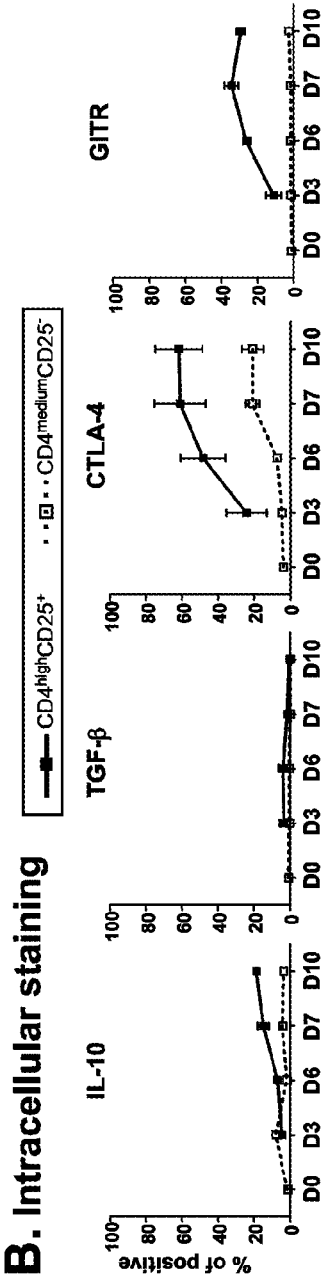

Alloantigen-specific CD4$^{high}$CD25$^+$Foxp3$^+$ Treg expressed CTLA-4 and GITR but had minimal secretion of TGF-β or IL-10 (FIG. 4). Other surface markers, such as CD27 and CD44, were previously reported by others to discriminate between functional Treg and non-Treg.[36,37] However, no significant difference was observed in the expression of CD27 and CD44 between the CD4$^{high}$CD25$^+$Foxp3$^+$Treg and CD4$^{medium}$CD25$^-$Foxp3$^-$ non-Treg produced with the B-cell co-culture system.

In certain embodiments, the suppressive effects of the alloantigen-specific Treg generated according to methods of the subject invention can occur with as little as about 718 suppressors (0.0156:1 ratio) in a culture of about 50,000 responding CD4$^+$CD25$^-$ T cells and about 50,000 allogeneic peripheral blood mononuclear cell (PBMC) stimulators. These effects are more potent than those previously reported for freshly isolated or expanded human polyclonal and alloantigen-specific Treg,[9-11,21] and again support the clinical utility of the Treg generated by CD40-activated B cells in adoptive immunotherapy.

Clinical Applications

The subject invention also provides methods for treating graft rejection or promoting graft survival or for treating or preventing autoimmune diseases or conditions.

In one embodiment, donor alloantigen-specific regulatory T cells are generated from a population of cells using a method of the present invention and are adoptively transferred or provided to a subject that has received a graft transplant or that will be receiving a graft transplant or that is suffering from, or may suffer from, an autoimmune disease or condition.

The autoimmune disease may be, for example, type I Diabetes, Addison's disease, lupus, rheumatoid arthritis, Graves disease, Multiple Sclerosis or Wegener's granulomatosis.

In one embodiment, the subject is a human and the donor alloantigen-specific regulatory T cells are human T cells. In one embodiment, the alloantigen-specific regulatory T cells are CD4$^{high}$CD25$^+$Foxp3$^+$ regulatory T cells.

Figure 5:
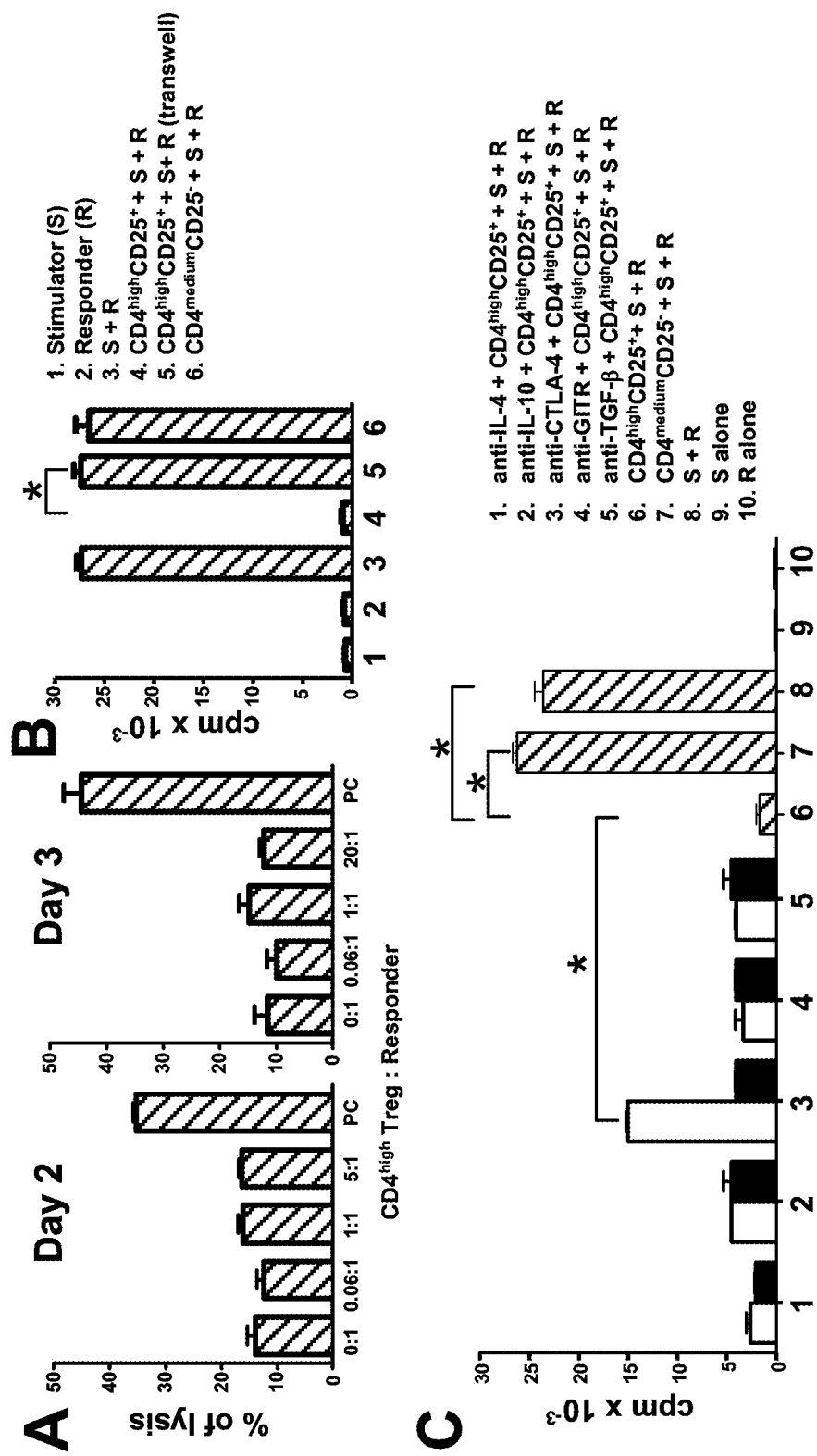
FIGS. 5A-C shows $CD4^{high}CD25^+$ alloantigen-specific Treg have no cytotoxic capacity and their suppressor function is dependent on cell-cell contact and partially relies on CTLA-4 expression. $CD4^{high}CD25^+$ Treg or $CD4^{medium}CD25^-$ T cells were sorted after 7 days of allo-stimulation as shown in FIG. 3B. (5A) Cytotoxic capacity of induced $CD4^{high}CD25^+$ Treg. (5B) The alloantigen-specific suppressor function of $CD4^{high}CD25^+$ Treg is cell-cell contact dependent. (5C) Neutralizing anti-CTLA-4 mAb partially reverses the alloantigen-specific suppression mediated by $CD4^{high}CD25^+$ Treg, but neutralizing mAbs to IL-4, IL-10, TGF-β and GITR fail to reverse that suppression. Responder (R) $CD4^+CD25^-$ and gamma-irradiated stimulator PBMC (S) were co-cultured with or without sorted $CD4^{high}CD25^+$ Treg or $CD4^{medium}CD25^-$ T cells. The cytotoxic activities (A) of human IL-2 activated NK cells against K562 cells were set as positive controls (PC). Stimulator (S) or responder (R) cells alone were set as controls. For transwell experiments (B), the same amount of responder (R) and stimulator (S) cells were plated in the bottom wells of a transwell system. The top well insert was inoculated with same amount of sorted $CD4^{high}CD25^+$ Treg. For the blocking experiments (C), the neutralization mAbs (open bars) and their relevant isotype controls (filled bars) were added in the co-culture system. Proliferation (y-axis) is shown for day 3 of cultures. Data for four different experiments are shown (n=4). The two-tailed unpaired Student's t tests were used for comparison. * indicate p<0.01.

Advantageously, the induced CD4$^{high}$CD25$^+$Foxp3$^+$ Treg of the subject invention did not have cytotoxic activities (FIG. 5). In addition, the possibility of involvement of Th2 response in MLR was excluded because blockade of IL-4 failed to inhibit the suppression of CD4$^{high}$CD25$^+$Foxp3$^+$ Treg (FIG. 5).

All patents, patent applications, provisional applications, and publications referred to or cited herein, subra or infra, are incorporated by reference in their entirety, including all figures and tables, to the extent they are not inconsistent with the explicit teachings of this specification.

Materials and Methods

Generation of CD40-activated B Cells

Human peripheral blood was obtained from healthy donors in accordance with ethical committee approval. PBMC were isolated by density gradient centrifugation as previously reports.[28,29] B cells from PBMC were stimulated via CD40 using NIH3T3 cells transfected with the human CD40 ligand (t-CD4O-L cells) as described previously.[27] The transfected cells have been stable for human CD4OL expression over a period of 5 yr, and no other human molecules are expressed on t-CD4O-L cells.[27] The lethally irradiated (96 Gy) t-CD40-L cells were plated on 6-well plates (Costar, Cambridge, Mass.) at a concentration of 0.4×10$^5$ cells/well in medium containing 45% DME (Gibco/BRL, Gaithersburg, Md.), 45% F12 (Gibco/BRL) 10% FCS, 2 mM glutamine (Gibco/BRL), and 15 ᵢug/ml gentamicin (Gibco/BRL).

After an overnight culture at 37° C. in 5% $CO_2$, t-CD4OL cells were adherent and ready for B-cell culture. PBMC at 2×10$^6$ cells/ml were co-cultured at 37° C. in 5% $CO_2$ with t-CD4OL cells in the presence of IL-4 (2 ng/ml; R&D systems, Minneapolis, Minn.) and cyclosporin A (CsA, 5.5× 10$^{-7}$M in Iscove's MDM (Gibco/BRL) supplemented with 10% human AB serum. 50 μg/ml transferrin (Boehringer Mannheim, Indianapolis, Ind.), 5 μg/ml insulin (Sigma Chemical Co., St. Louis, Mo.), and 15 μg/ml gentamicin (Gibco/BRL).

The concentration of CsA used here was found to only suppress T-cell proliferation without affecting B-cell growth. Cultured cells were transferred to the wells of new plates with fresh irradiated t-CD40-L cells every 3-5 d. Once the cultured PBMC were 75% CD19, they were cultured at concentrations of 0.75-1.0×10$^6$ cells/ml. The number of viable cells, and CD19$^+$B cells were analyzed by flow cytometry every 3-5 d. After 14 days of co-culture, more than 95% of the viable suspended cells are CD19 positive. B cells were cryopreserved for future use. For co-culture with CD4$^+$ T cells, the cryopreserved CD40-activated B cells were always centrifuged on a Ficoll-Hypaque density gradients and washed twice in PBS to remove nonviable cells including remaining t-CD40L cells. Alternatively, t-CD40L cells were replaced by different concentrations of the soluble hexameric CD40L (sCD40L, Alexis Biochemicals, Switzerland) to expand B cells as above.[30]

T-cell Isolation

Human CD4$^+$ or naïve CD4$^+$ T cells were isolated from healthy donor PBMC by negative selection using a CD4$^+$ T-cell isolation kit or a naïve CD4$^+$ T-cell isolation kit (Miltenyi Biotec, Calif.) for depletion of cells expressing CD8, CD 14, CD 16, CD 19, CD36, CD56, CD123, TCRγ/δ and CD235a (glycophorin A) (for CD4+T cells) or depletion of CD8, CD14, CD16, CD19, CD36, CD56, CD123, TCRγ/δ, CD235a and CD45RO (for naïve CD4$^+$ T cells). The CD25$^+$ cells were further depleted by positive selection with directly conjugated anti-CD25 magnetic microbeads (Miltenyi Biotec, Calif.) following the double-column depletion procedures. After the double-column depletion procedure, the CD4*CD25⁻ or CD4⁺CD45RA⁺CD45RO⁻CD25⁻ cells were routinely more than 99% pure by flow cytometry analysis. In some cases, the CD25⁻ cells were sorted by FACSAria, and the purity of CD4⁺CD25⁻ or CD4⁺CD45RA⁺CD45RO⁻ CD25⁻ cells was greater than 99.9%.

Allogeneic Stimulation Assay to Induce and Expand Treg

Freshly purified CD4⁺CD25⁻ or CD4⁺CD45RA⁺ CD45RO⁻CD25⁻T cells were co-cultured with allogeneic CD40-activated B cells at a 10:1 T- to B-cell ratio in the RPMI 1640 medium with 10% heat-inactivated human AB serum. For some experiments, the T cells were labeled with CFSE as previously reported before co-culture with CD40-activated B cells.[18] In the repeated stimulation experiments, the allogeneic CD40-activated B cells were added every 7 days of culture. In some experiments, human recombinant IL-2 (1000 IU/ml) was added in the culture medium. Functional and phenotypical hallmarks of the induced and expanded T cells were examined at the indicated time of culture. The expansion of the cells was determined by counting trypan blue-excluding cells.

Flow Cytometry Analysis

Cells were phenotypically analyzed using a FACSAria. The following fluorescence-conjugated mAbs were used. Anti-CD4-PE-Cy5, anti-CD45RA-PE, anti-CD45RO-APC were purchased from Caltag Laboratories-Invitrogen (Carlsbad, Calif.). Anti-CD25-APC, antiCD62L-APC, anti-CD27-PE, anti-CD44-PE, anti-CCR7-PE, anti-CTLA-4-PE, anti-GITR-PE and their isotype-matched control Abs of irrelevant specificity were purchased from BD Biosciences. Intracellular staining was performed after cell fixation and permeabilization, using Fix and Perm reagents (BD Biosciences) as we reported before.[28,29][31] The following mAbs were used: anti-CTLA-4-PE (BD Biosciences), anti-GITR-PE (BD Biosciences), anti-IL-10-PE (R&D), anti-TGF-fl-PE (IQ-products, Netherlands), and anti-IL-2 (BD Biosciences). For Foxp3 staining, the human Foxp3 staining kit (eBiosciences) was used as we described before.[32]

Mixed Lymphocyte Reaction (MLR) Assays

The suppressor capacity of T cells induced and expanded in co-culture with allogeneic CD40-activated B cells was studied in an MLR co-culture suppression assay, as we described before with some modifications.[23,32] CD4⁺CD25⁻ or CD4⁺ CD45RA⁺CD25⁺T cells were co-cultured with allogeneic CD40-activated B cells (target) for 7 or 21 days, after which time $CD4^{medium}CD25^-$ and $CD4^{high}CD25^+$T cells were sorted by FACSAria. The purity of sorted cells was routinely more than 99%. The sorted $CD4^{high}CD25^+$ and $CD4^{medium}CD25^+$ cells referred to as "suppressor" were titrated and added at the start of MLR assays, consisting of a total of $5^{33}$ 10⁴ responder CD4⁺CD25⁻ T cells from same donor of $CD4^{medium}/CD4^{high}$ cells and 5×10⁴ gamma-irradiated (30 Gy) target PBMC from same donor of allogeneic B cells. Antigen specificity was examined in the co-cultures that were performed with third-party stimulator PBMC that were fully class I and II HLA-mismatched with the (target) allogeneic B cells. Proliferation was analyzed by [³H]-thymidine incorporation assay as described previously,[33,34] with incorporation expressed as the mean ±SEM cpm of four to six wells/condition.

Cytotoxic capacity of the induced and expanded cells was detenoined by the Live/Dead cell-mediated cytotoxicity kit (Molecular Probes, Oreg.).[35] Similar MLR co-culture was set except responder CD4⁺CD25⁻ T cells were labeled with 3,3'-dioctadecyloxacarbocyanine (DiO). After 2 and 3 days of MLR culture, cells were stained with propidium iodide (PI) at 37° C. for 2 h, and then analyzed by flow cytometry. Back gating on the green fluorescent target cells, the PI-positive cells were evaluated for the percentage of lysed cells.

The contact dependency of $CD4^{high}CD25^+$ Treg was examined in Transwell experiments using 24-well plates. Briefly, 2×10⁵ responder CD4⁺CD25⁻ cells and 2×10⁵ gamma-irradiated stimulator PBMC (target) were co-cultured in the lower compartment of the well. 2×10⁵ of $CD4^{high}CD25^+$ Treg were cultured in the Transwell insert (0.4 um pore size; Millicell; Millipore). On day 3 of the co-cultures, equivalent culture volumes were transferred from the lower compartment of the 24-well plate to a 96-well, round-bottom plate and analyzed for proliferation as above.

Blocking studies were performed in the presence of the neutralization mAbs directly against CTLA-4 (10 µg/ml, Ancell, USA), IL-4 (10 µg/ml, R&D), IL-10 (10 µg/ml, eBiosciences), GITR (2 µg/ml, R&D), TGF-β (2 µg/ml, R&D) and their relevant isotype controls.

Statistical Analysis

Graphs and statistical analyses were performed with the use of Prism 4.00 for Windows software (GraphPad Software, San Diego, Calif.). P values of 0.05 or less were considered significant.

EXAMPLE 1

CD40-activated B Cells Expanded by Incubation with Either CD40-ligand Transfected Cells or Soluble Hexameric CD40-ligand Express High Levels of MHC and Co-stimulatory Molecules As in a previous report,[27] non-transformed CD40-activated B cells could be expanded from circulating B cells contained in PBMC by treatment with CD40-ligand (CD40-L) transfected NIH3T3 (t-CD40-L) cells, IL-4, and low concentrations of cyclosporin A. The purity of CD19⁺CD3⁻B cells was at least 83% by day 8, and more than 95% at day 12. By 28-32 days of culture, more than 99% of cells were the CD19⁺ CD3⁻B cells. To evaluate the expansion rate of B cells, we monitored the absolute number of CD19⁺CD3⁻ cells generated from 5.0 ml of peripheral blood from 8 unselected healthy adult donors. We found that after 32 days of culture, 8.1-54.3×10⁷ CD40-activated B cells could be generated (FIG. 1A). We next determined if soluble hexameric CD40-ligand (sCD40-L) could replace t-CD40-L for B-cell activation and expansion, as t-CD40-L are xenogenic and would be potentially undesirable contaminants in adoptive immunity protocols in humans. We found that sCD40-L expanded B cells in a dose-dependent fashion (FIG. 1B). At the concentration of 1.0 µg/ml, it was similarly effective as t-CD40-L in promoting B-cell expansion (FIG. 1B). CD40-activated B cells generated using either sCD40-L or tCD40-L expressed high levels of MHC class I and II molecules and costimulatory molecules CD80 and CD86 at 8 days (FIG. 1C) and the expression of these molecules remained stable thereafter.

EXAMPLE 2

Human Alloreactive $CD4^{high}$ Cells Induced by CD40-activated B Cells are Treg To determine whether allogeneic CD40-activated B cells can induce Treg from CD4⁺CD25⁻ T cells, purified circulating CD4⁺CD25⁻ T cells (purity >99%) were stimulated with allogeneic CD40-activated B cells for 7 days. Surprisingly, a new cell subset with significantly upregulated levels of CD4 surface expression was induced after 5 days of allostimulation, and most of these $CD4^{high}$ cells lost CD45RA expression (FIG. 2A) and acquired CD45RO expression (data not shown). Furthermore, most of these CD4$^{high}$ cells also lost CFSE staining while the CD4$^{medium}$ cells still maintained their CFSE content (FIG. 2A), suggesting that the induced CD4$^{high}$ cells were proliferating alloreactive cells. These presumed alloreactive CD4$^{high}$ cells expressed CD25 and Foxp3, while CD4$^{medium}$ cells did not express these two Treg markers (FIG. 2B). Together, these findings indicated that CD40-activated B cells preferentially expanded a CD4$^{high}$CD25$^+$Foxp3$^+$Treg cell population. Similar results were also found using highly purified CD4$^+$CD25$^-$T cells (purity >99.9%) sorted by FACS in this co-culture system (data not shown). Thus, it is unlikely that the CD4$^{high}$CD25$^+$Foxp3$^+$ Treg obtained were the result of an expansion of CD4$^+$CD25$^+$ T cells contaminating the initial culture.

To examine the function and alloantigen specificity of the induced CD4$^{high}$ CD25$^+$Foxp3$^+$ Treg from CD4$^+$CD25$^-$ cells, the MLR assay was used. As shown in FIG. 2C, after 7 days of allostimulation, CD4$^{high}$CD25$^+$ and CD4$^{medium}$CD25$^-$ cells were sorted by FACS and then added in the MLR assay. CD4$^{medium}$ cells did not suppress either the original target or third-party alloantigen-induced proliferation, whereas CD4$^{high}$CD25$^+$ cells suppressed both target- and third-party-antigen induced proliferations, although their suppressive effect on third-party alloantigen-induced proliferation was lower than that mediated by the target alloantigen (FIG. 2C). Thus, CD4$^{high}$CD25$^+$ Treg generated from CD4$^+$CD25$^-$ cells effectively suppressed in the MLR assay, but their suppression was not alloantigen-specific.

EXAMPLE 3

CD40-activated B Cells can Induce Alloantigen-specific CD4$^{high}$CD25$^+$ Treg from Naïve CD4$^+$CD25$^-$ Cells We next determined if alloantigen-specific Treg could be generated from purified naïve CD4$^+$CD25$^-$ cells (CD4$^+$CD45RA$^+$CD45RO$^-$CD25$^+$) by co-culture with allogeneic CD40-activated B cells. As in the case of unfractionated CD4$^+$CD25$^-$T cells, naive CD4$^±$CD25$^-$ cells expanded by co-culture with CD40-activated B cells also acquired a CD4$^{high}$, CD25$^+$ and Foxp3$^+$ phenotype after 7 days of culture, (FIG. 3A). Furthermore, these CD4$^{high}$CD25$^+$Foxp3$^+$ Treg underwent 7-8 cells divisions by 7 days of allostimulation (FIG. 3A). In contrast, CD4$^{medium}$ cells neither divided nor expressed CD25 and Foxp3 (FIG. 3A).

We further examined the suppressive capacity and alloantigen specificity of the CD4$^{high}$CD25$^+$ Treg induced from naive precursors. These CD4$^{high}$CD25$^+$ Treg significantly suppressed the original target alloantigen-induced proliferation, whereas CD4$^{medium}$CD25$^-$ cells did not show substantial suppressive ability (FIG. 3B). Importantly, the induced CD4$^{high}$CD25$^+$ Treg were unable to suppress a third-party alloantigen-induced proliferation (FIG. 3B). These data demonstrate that CD4$^{high}$CD25$^+$ Treg induced from naive CD4$^+$CD25$^-$ T cells by allogeneic CD40-activated B cells are alloantigen-specific.

The CD4$^{high}$CD25$^+$ Treg generated from naive precursors had very high suppressive potential: Even at a cell ratio of 1:256 for Treg:responder cells (CD4$^+$CD25$^-$), there was approximately 50% suppression of target alloantigen-stimulated proliferation. At a Treg to responder cells ratio of 1:16 or higher, the target alloantigen-stimulated proliferation was almost completely inhibited (FIG. 3B). This highly suppressive potential was also evident with unsorted CD4$^+$ T cells containing approximately 80% of CD4$^{high}$CD25$^+$ T cells and 20% of CD4$^{medium}$CD25$^-$T cells, indicating that contaminating CD4$^{medium}$CD25$^-$ cells do not interfere with Treg activity and therefore do not need to be removed by FACS sorting (FIG. 3B).

EXAMPLE 4

Characteristics of CD4$^{high}$CD25$^+$Foxp3$^+$Alloantigen-specific Treg

We further characterized the phenotype of the induced CD4$^{high}$CD25$^+$Foxp3$^+$ alloantigen-specific Treg population. CD25 was significantly upregulated from low basal levels by day 3 of culture, and more than 90% and 95% of CD4$^{high}$ cells expressed CD25 at day 3 and day 10 respectively, whereas there was no CD25 upregulation on CD4$^{medium}$ cells for up to 10 days of culture (FIG. 4A). The memory T-cell marker CD45RO was also upregulated in both CD4$^{high}$ and CD4$^{medium}$ cells, but while 95% of CD4$^{high}$ cells were CD45RO after 10 days of culture and only about 50% of CD4$^{medium}$ cells had this surface phenotype. Unlike previous reports indicating that the expression of CD27 and CD44 can discriminate functional CD4+CD25+Treg in human and mice,[36,37] we found no significant differences in CD27 and CD44 surface expression by CD4$^{high}$ Treg compared to CD4$^{medium}$ T cells or within the population of CD4$^{high}$CD25$^+$ Treg (FIG. 4A). Most of induced CD4$^{high}$ Treg lost their CCR7 expression after 6 days of culture, suggesting they had a memory/effector like phenotype and tendency to migrate to inflamed tissues rather than undergo recirculation between the lymph nodes and blood.[38] However, CD4$^{high}$ Treg still maintained high levels of CD62L expression, which likely would confer effective lymph node homing via high endothelial venules.

We next examined the expression of proteins previously implicated in the suppressive activity of Treg, including cytotoxic T lymphocyte antigen-4 (CTLA-4 or CD 152), glucocorticoid-induced TNF receptor (GITR), IL-10 and TGF-β.[39] FIG. 4 shows that cell surface CTLA-4 and GITR were clearly detectable by day 3 and gradually increased such that about 30% and 45% of CD4$^{high}$ Treg expressed surface CTLA-4 and GITR, respectively, between day 6 and day 7. This was followed by a gradual decline in surface expression. Total CTLA-4 and GITR expression displayed different kinetics in that they gradually increased from day 3 so that about 60% and 30% of CD4$^{high}$CD25$^+$ Treg expressed CTLA-4 and GITR, respectively, after 10 days of culture based on intracellular staining (FIG. 4B). In contrast, CD4$^{medium}$CD25$^-$ T cells expressed little or no CTLA-4 and GITR molecules on the surface or intracellularly (FIG. 4). Both CD4$^{medium}$CD25$^-$ cells and CD4$^{high}$CD25$^+$ Treg expressed little or no detectable IL-10 and TGF-β during 10 days of culture (FIG. 4B). Taken together, these data suggest that CTLA-4 or GITR but not 1L-10 and TGF-β are potential mediators of CD4$^{high}$CD25$^+$ Treg suppressive activity.

EXAMPLE 5

CD4$^{high}$CD25$^+$ Treg Lack Cytotoxic Capacity and Suppress by a Mechanism that Requires Cell-cell Contact and Involves, in Part, CTLA-4 Expression To determine the mechanism of CD4$^{high}$CD25$^+$ Treg suppression, we first determined whether CD4$^{high}$CD25$^+$ alloantigen-specific Treg had cytotoxic activity to responder cells (CD4$^+$CD25$^-$), as previous studies demonstrated that the suppression of Treg was dependent on their cytotoxicity.[40,41]

CD4$^{high}$CD25$^+$ Treg did not kill responder cells or induce their apoptosis during 2-3 days of MLR (FIG. 5A), suggesting that the suppression of CD4$^{high}$CD25$^+$ alloantigen-specific Treg was not mediated by cell-mediated cytotoxicity.

We next determined if CD4$^{high}$CD25$^+$ suppression could be mediated solely by soluble molecules released from Treg. As shown in FIG. 5B, the suppression was lost when the responder cells were physically separated from the induced CD4$^{high}$CD25$^+$ Treg in a transwell culture system. The addition of neutralizing monoclonal antibodies (mAb) for IL-10, TGF-β, IL-4 or GITR into MLR cultures had little or no effect on the ability of CD4$^{high}$CD25$^+$ Treg to suppress alloantigen-specific proliferation (FIG. 5C). In contrast, antibody blockade of CTLA-4 partially reversed CD4$^{high}$CD25$^+$ Treg suppression (FIG. 5C). Together, these data suggest that the CD4$^{high}$CD25$^+$ Treg-mediated suppression of alloantigen responses is cell-cell contact dependent and mediated, in part, by CTLA-4.

EXAMPLE 6

CD4$^{high}$CD25$^+$ Treg can be Continuously Expanded by CD40-activated B Cells in Large-scale Without Loss of Function and Exogenous IL-2 Does Not Enhance Cell Expansion We examined the ability of three weeks of co-culture of naïve CD4$^+$CD25$^-$ T cells with allogeneic CD40-activated B cells to generate Treg, in which freshly generated CD40-activated B cells were added weekly. As shown in FIG. 6A, CD4$^{high}$CD25$^+$ Treg gradually increased, and more than 92% of T cells in culture were the CD4$^{high}$CD25$^+$ Treg at day 21 (FIG. 6A). Using ten healthy randomly selected adult blood donors, we were able to expand CD4$^{high}$CD25$^+$ Treg 6.4× 10$^5$- to 1.6×10$^7$-fold during 21 days of culture (FIG. 6B). This expansion did not require exogenous IL-2, as its addition did not increase the generation of CD4$^{high}$CD25$^+$Treg cells (FIG. 6C). To more precisely determine the rate of expansion, we used a standard number of naïve CD4$^+$CD25$^-$ T cells (1×10$^6$) at the beginning of the culture, and found that about 8.3×10$^6$ (range from 5.4-11.3×10$^6$) of CD4$^{high}$CD25$^+$Treg could be generated from every 1×10$^6$ of naïve CD4$^+$CD25$^-$ T cells in ten unselected donors (FIG. 6D). Furthermore, expanded CD4$^{high}$CD25$^+$ Treg evaluated at 21 days of culture had similar suppressive ability and alloantigen specificity (FIG. 6E) as Treg generated over a shorter period of in vitro culture. In addition, these Treg still maintained their high levels of Foxp3 expression (data not shown). Together, these results demonstrate that CD40-activated B cells can induce and expand CD4$^{high}$CD25$^+$Foxp3$^+$ alloantigen-specific Treg at a scale that is likely to be relevant for clinical immunotherapy.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

It should be understood that the examples and embodiments described herein are for illustrative purposes only and that various modifications or changes in light thereof will be suggested to persons skilled in the art and are to be included within the spirit and purview of this application.

BIBLIOGRAPHY

1. Joffre O, van Meerwijk J P. CD4(+)CD25(+) regulatory T lymphocytes in bone marrow transplantation. Semin Immunol. 2006;18:128-135.
2. Tarbell K V, Yamazaki S, Steinman R M. The interactions of dendritic cells with antigen-specific, regulatory T cells that suppress autoimmunity. Semin Immunol. 2006;18:93-102.
3. Waldmann H, Chen T C, Graca L, et al. Regulatory T cells in transplantation. Semin Immunol. 2006;18:111-119.
4. Salomon B, Lenschow D J, Rhee L, et al. B7/CD28 costimulation is essential for the homeostasis of the CD4+ CD25+ immunoregulatory T cells that control autoimmune diabetes. Immunity. 2000;12:431-440.
5. Edinger M, Hoffmann P, Ermann J, et al. CD4+CD25+ regulatory T cells preserve graft-versus-tumor activity while inhibiting graft-versus-host disease after bone marrow transplantation. Nat Med. 2003;9:1144-1150.
6. Taylor P A, Lees C J, Blazar B R. The infusion of ex vivo activated and expanded CD4(+)CD25(+) immune regulatory' cells inhibits graft-versus-host disease lethality. Blood. 2002;99:3493-3499.
7. Kang S M, Tang Q, Bluestone J A. CD4+CD25+ regulatory T cells in transplantation: progress, challenges and prospects. Am J Transplant. 2007;7:1457-1463.
8. Sanchez-Fueyo A, Domenig C M, Mariat C, Alexopoulos S, Zheng X X, Strom T B. Influence of direct and indirect allorecognition pathways on CD4+CD25– regulatory T-cell function in transplantation. Transpl Int. 2007;20: 534-541.
9. Godfrey W R, Ge Y G, Spoden D J, et al. In vitro-expanded human CD4(±)CD25(+) T-regulatory cells can markedly inhibit allogeneic dendritic cell-stimulated MLR cultures. Blood. 2004;104:453-461.
10. Hoffmann P, Eder R, Kunz-Schughart L A, Andreesen R, Edinger M. Large-scale in vitro expansion of polyclonal human CD4(+)CD25high regulatory T cells. Blood. 2004; 104:895-903.
11. Levings M K, Sangregorio R, Roncarolo M G. Human cd25(±)cd4(+) t regulatory cells suppress naive and memory T cell proliferation and can be expanded in vitro without loss of function. J Exp Med. 2001:193:1295-1302.
12. Taylor P A, Panoskaltsis-Mortari A, Swedin J M, et al. L-Selectin(hi) but not the Lselectin(lo) CD4+25+ T-regulatory cells are potent inhibitors of GVHD and BM graft rejection. Blood. 2004;104:3804-3812.
13. Tang Q, Henriksen K J, Bi M, et al. In vitro-expanded antigen-specific regulatory T cells suppress autoimmune diabetes. J Exp Med. 2004;199:1455-1465.
14. Joffre O, Santolaria T, Calise D, et al. Prevention of acute and chronic allograft rejection with CD4+CD25+Foxp3– regulatory T lymphocytes. Nat Med. 2008;14:8892.
15. Trenado A, Charlotte F, Fisson S, et al. Recipient-type specific CD4+CD25+ regulatory T cells favor immune reconstitution and control graft-versus-host disease while maintaining graft-versus-leukemia. J Clin Invest. 2003; 112:1688-1696.
16. Bushell A, Jones E, Gallimore A, Wood K. The generation of CD25+CD4$^+$ regulatory T cells that prevent allograft rejection does not compromise immunity to a viral pathogen. J Immunol. 2005;174:3290-3297.

17. Nguyen V H, Shashidhar S, Chang D S, et al. The impact of regulatory T cells on T-cell immunity following hematopoietic cell transplantation. Blood. 2008;111:945953.
18. Golshayan D, Jiang S. Tsang J, Garin M I, Mottet C, Lechler R I. In vitro-expanded donor alloantigen-specific CD4CD25+ regulatory T cells promote experimental transplantation tolerance. Blood. 2007;109:827-835.
19. Yamazaki S, Patel M, Harper A, et al. Effective expansion of alloantigen-specific Foxp3+CD25−+CD4+ regulatory T cells by dendritic cells during the mixed leukocyte reaction. Proc Natl Acad Sci U S A. 2006;103:2758-2763.
20. Kretschmer K, Apostolou I, Hawiger D, Khazaie K, Nussenzweig M C, von Boehmer H. Inducing and expanding regulatory T cell populations by foreign antigen. Nat Immunol. 2005;6:1219-1227.
21. Walker M R, Carson B D, Nepom G T, Ziegler S F, Buckner J H. De novo generation of antigen-specific CD4+CD25+ regulatory T cells from human CD4+CD25− cells. Proc Natl Acad Sci U S A. 2005;102:4103-4108.
22. Garderet L, Cao H, Salamero J, et al. In vitro production of dendritic cells from human blood monocytes for therapeutic use. J Hematother Stem Cell Res. 2001;10:553-567.
23. Liu E, Tu W, Law H K, Lau Y L. Decreased yield, phenotypic expression and function of immature monocyte-derived dendritic cells in cord blood. Br J Haematol. 2001; 113:240-246.
24. Finkelman. F D, Lees A, Birnbaum R, Gause W C, Morris S C. Dendritic cells can present antigen in vivo in a tolerogenic or immunogenic fashion. J Immunol. 1996;157: 1406-1414.
25. Ardeshna K M, Pizzey A R, Walker S J, Devereux S, Khwaja A. The upregulation of CC chemokine receptor 7 and the increased migration of maturing dendritic cells to macrophage inflammatory protein 3beta and secondary lymphoid chemokine is mediated by the p38 stress-activated protein kinase pathway. Br J Haematol. 2002;119: 826-829.
26. von Bergwelt-Baildon M S, Vonderheide R H, Maecker B, et al. Human primary and memory cytotoxic T lymphocyte responses are efficiently induced by means of CD40-activated B cells as antigen-presenting cells: potential for clinical application. Blood. 2002;99:3319-3325.
27. Schultze J L, Michalak S, Seamon M J, et al. CD40-activated human B cells: an alternative source of highly efficient antigen presenting cells to generate autologous antigen-specific T cells for adoptive immunotherapy. J Clin Invest. 1997;100:27572765.
28. Tu W, Chen S, Sharp M, et al. Persistent and selective deficiency of CD4−, T cell immunity to cytomegalovirus in immunocompetent young children. J Immunol. 2004;172: 3260-3267.
29. Tu W, Potena L, Stepick-Biek P, et al. T-cell immunity to subclinical cytomegalovirus infection reduces cardiac allograft disease. Circulation. 2006;114:1608-1615.
30. Holler N, Tardivel A, Kovacsovics-Bankowslii M, et al. Two adjacent trimeric Fas ligands are required for Fas signaling and formation of a death-inducing signaling complex. Mol Cell Biol. 2003;23:1428-1440.
31. Chen S F, Tu W W, Sharp M A, et al. Antiviral CD8 T cells in the control of primary human cytomegalovirus infection in early childhood. J Infect Dis. 2004;189:1619-1627.
32. Cohen A C, Nadeau K C, Tu W, et al. Cutting edge: Decreased accumulation and regulatory function of CD4+CD25(high) T cells in human STAT5b deficiency. J Immunol. 2006;177:2770-2774.
33. Tu W, Cheung P T, Lau Y L. IGF-I increases interferon-gamma and IL-6 mRNA expression and protein production in neonatal mononuclear cells. Pediatr Res. 1999;46:748-754.
34. Tu W, Zhang D K, Cheung P T, Tsao S W, Lau Y L. Effect of insulin-like growth factor 1 on PHA-stimulated cord blood mononuclear cell telomerase activity. Br J Haeatol. 1999;104:785-794.
35. Chang L, Gusewitch G A, Chritton D B, Folz J C, Lebeck L K, Nehlsen-Cannarella S L. Rapid flow cytometric assay for the assessment of natural killer cell activity. J Immunol Methods. 1993;166:45-54.
36. Koenen H J, Fasse E, Joosten I. CD27/CFSE-based ex vivo selection of highly suppressive alloantigen-specific human regulatory T cells. J Immunol. 2005;174:7573-7583.
37. Firan M, Dhillon S, Estess P, Siegelman M H. Suppressor activity and potency among regulatory T cells is discriminated by functionally active CD44. Blood. 2006;107:619-627.
38. Sallusto F, Lenig D, Forster R, Lipp M, Lanzavecchia A. Two subsets of memory T lymphocytes with distinct homing potentials and effector functions. Nature. 1999;401: 708-712.
39. Jiang S, Lechler R I. Regulatory T cells in the control of transplantation tolerance and autoimmunity. Am J Transplant. 2003;3:516-524.
40. Grossman W J, Verbslky J W, Barchet W, Colonna M, Atkinson J P, Ley T J. Human T regulatory cells can use the perforin pathway to cause autologous target cell death. Immunity. 2004;21:589-601.
41. Pandiyan P, Zheng L, Ishihara S, Reed J, Lenardo M J. CD4+CD25−Foxp3+ regulatory T cells induce cytokine deprivation-mediated apoptosis of effector CD4+ T cells. Nat Immunol. 2007;8:1353-1362.
42. Jonuleit H. Schmitt E, Schuler G, Knop J, Enk A H. Induction of interleukin 10-producing, nonproliferating CD4(+) T cells with regulatory properties by repetitive stimulation with allogeneic immature human dendritic cells. J Exp Med. 2000;192:1213-1222.
43. von Bergwelt-Baildon M, Shimabukuro-Vornhagen A, Popov A, et al. CD40-activated B cells express full lymph node homing triad and induce T-cell chemotaxis: potential as cellular adjuvants. Blood. 2006;107:2786-2789.
44. Zhong X, Gao W, Degauque N, et al. Reciprocal generation of Th1/Th17 and T(reg) cells by B1 and B2 B cells. Eur J Immunol. 2007;37:2400-2404.
45. Walker M R, Kasprowicz D J, Gersuk V H, et al. Induction of FoxP3 and acquisition of T regulatory activity by stimulated human CD4+CD25− T cells. J Clin Invest. 2003;112: 1437-1443.
46. Fontenot J D, Rasmussen J P, Gavin. M A, Rudensky A Y. A function for interleukin 2 in Foxp3-expressing regulatory T cells. Nat Immunol. 2005;6:1 142-1151.
47. Ermann J, Hoffmann P, Edinger M, et al. Only the CD62L+ subpopulation of CD4+CD25+ regulatory T cells protects from lethal acute GVHD. Blood. 2005;105:2220-2226.
48. Read S, Malmstrom V, Powrie F. Cytotoxic T lymphocyte-associated antigen 4 plays an essential role in the function of CD25(+)CD4(+) regulatory cells that control intestinal inflammation. J Exp Med. 2000;192:295-302.
49. Talkahashi T, Tagami T, Yamazaki S, et al. Immunologic self-tolerance maintained by CD25($-^L$)CD4(+) regulatory T cells constitutively expressing cytotoxic T lymphocyte-associated antigen 4. J Exp Med. 2000;192:303-310.

50. Sayegh M H, Weiner H L. Regulating rejection with cell therapy. Nat Biotechnol. 2008;26:191-192.

What is claimed is:

1. A method for preventing a human patient from rejecting an organ or tissue transplant from a donor due to allograft rejection, comprising:
   - obtaining a sample of naïve $CD4^+CD25^-$ T-cells from the patient;
   - co-culturing allogeneic CD40-activated B cells from the donor with the naïve $CD4^+CD25^-$ T cells from the patient in a ratio of 1:10 in the absence of exogenous cytokines for a period of time sufficient to generate alloantigen-specific human regulatory T cells; and
   - administering the alloantigen-specific human regulatory T cells to the patient.

2. The method according to claim 1, wherein the alloantigen-specific human regulatory T cells comprise $CD4^{high}CD25^+Foxp3^+$ regulatory T cells.

3. The method according to claim 1, wherein the period of time is about 21 days.

4. The method according to claim 1, further comprising obtaining the naïve $CD4^+CD25^-$ T cells from peripheral blood from the patient.

5. The method according to claim 1 further comprising generating a population of from about $6.4 \times 10^5$ to about $1.6 \times 10^7$ of the alloantigen-specific human regulatory T cells.

6. The method according to claim 1, further comprising generating a population $6.4 \times 10^5$ to about $1.6 \times 10^7$ of the alloantigen-specific human regulatory T cells that are $CD45RO^+$ and $CCR7^+$ memory cells.

* * * * *